(12) United States Patent
Winchester, Jr. et al.

(10) Patent No.: US 7,610,080 B1
(45) Date of Patent: Oct. 27, 2009

(54) METHOD AND DEVICE FOR DETERMINING TENSION IN LIGAMENTS AND TENDONS

(75) Inventors: Leonard W. Winchester, Jr., Yorktown, VA (US); Nee-Yin Chou, Yorktown, VA (US)

(73) Assignee: WinTec, LLC, Yorktown, VA (US)

( * ) Notice: Subject to any disclaimer, the term of this patent is extended or adjusted under 35 U.S.C. 154(b) by 605 days.

(21) Appl. No.: 10/703,436

(22) Filed: Nov. 10, 2003

Related U.S. Application Data

(60) Provisional application No. 60/424,690, filed on Nov. 8, 2002.

(51) Int. Cl.
*A61B 5/05* (2006.01)
*A61B 6/00* (2006.01)

(52) U.S. Cl. .................. 600/473; 600/476; 600/477; 600/407

(58) Field of Classification Search ............... 600/473, 600/476, 477, 407
See application file for complete search history.

(56) References Cited

U.S. PATENT DOCUMENTS

| | | | | |
|---|---|---|---|---|
| 4,669,467 | A * | 6/1987 | Willett et al. ................ | 606/7 |
| 5,615,673 | A * | 4/1997 | Berger et al. ................ | 600/326 |
| 5,991,653 | A | 11/1999 | Richards-Kortum et al. | |
| 6,486,948 | B1 * | 11/2002 | Zeng ........................ | 356/301 |
| 6,707,548 | B2 * | 3/2004 | Kreimer et al. .............. | 356/301 |
| 6,725,082 | B2 * | 4/2004 | Sati et al. ................... | 600/429 |
| 6,934,576 | B2 * | 8/2005 | Camacho et al. ............. | 600/473 |

FOREIGN PATENT DOCUMENTS

JP    11014470 A   *   1/1999

OTHER PUBLICATIONS

Cribb et al., Tendon Response to Tensile Stress: An Ultrastructural Investigation of Collagen:Proteoglycan Interactions in Stressed Tendon, J. Anat. (1995) 187, pp. 423-428.*
B.D. Beynnon and B.C. Fleming; *Anterior cruciate ligament strain in-vivo: A review of previous work*; J. Biomech., 31; pp. 519-525, 1998.

(Continued)

*Primary Examiner*—Brian Casler
*Assistant Examiner*—James Kish
(74) *Attorney, Agent, or Firm*—James Creighton Wray; Meera P. Narasimhan

(57) ABSTRACT

Infrared and Raman spectroscopy methods are used to assess the tension of ligaments, tendons and other tissue. The device includes an electromagnetic radiation source for directing radiation energy onto a sample, either directly or using a probe. Between the radiation source and the sample, emitted electromagnetic energies pass through a filtering device and are directed to the sample using optical components such as mirrors, lenses and optical fibers. After impacting the tissue, scattered emissions are collected by a collecting lens at a predetermined geometry. The scattered emissions are collected by a collection means such as lens and optical fibers directed to another filtering device and a spectrum-analyzing device, and detected with a photon-detecting device. The collected scattering signals are analyzed using a computing device such as a computer or a microprocessor. The tension in the tissue is obtained from the analysis of the scattered emissions.

42 Claims, 3 Drawing Sheets

OTHER PUBLICATIONS

Butler, D.L.; *Anterior cruciate ligament: its normal response and replacement*; J. Orthoped. Res., 7; pp. 910-921; 1989.

Frank, C.B. and D.W. Jackson; *The science of reconstruction of the anterior cruciate ligament*; J Bone Joint Surg., 79-A; pp. 1556-1576; 1997.

Frushour, B.G. and J.L. Koenig; *Raman scattering of collagen, gelatin, and elastin*; Biopolymers, 14; pp. 379-391; 1975.

Graf et al.; *Effect of preconditioning on the viscoelastic response of primate patellar tendon*; Arthroscopy 10; pp. 90-96; 1994.

Heck et al.; *Revision rates after knee replacement in the United States*; Med. Care, 36; pp. 661-669; 1998.

More, R.C. and K.L. Markolf; *Measurement of stability of the knee and ligament force after implantation of a synthetic anterior cruciate ligament: In vitro measurement*; J. Bone Joint Surg., 70-A; pp. 1020-1031; 1988.

Noyes, F.R. and E.S. Grood; *The strength of the anterior cruciate ligament in humans and rhesus monkeys*; J. Bone Joint Surg., 58A; pp. 1074-1082; 1976.

Rodeo et al.; *Tendon-healing in a bone tunnel*; J. Bone Joint Surg., 75-A; pp. 1795-1803; 1993.

Sachs et al; *Complications of Knee Ligament Surgery*; in "Knee Ligaments: Structure, Function, Injury, and Repair", edited by D.M. Daniel, W.H. Akeson, and J.J. O'Connor; Raven Press, Ltd., New York,Ch. 28; pp. 505-520; 1990.

Vergis, A. and J. Gillquist; *Graft failure in intra-articular anterior cruciate ligament reconstructions: A review of the literature*; Arthroscopy, 11; pp. 312-321; 1995.

Wang et al.; *Determination of molecular changes in soft tissues under strain using laser Raman microscopy*; J. Biomechanics, 33; pp. 483-486; 2000.

Woo, S.L.Y. and D.J. Adams; *The Tensile Properties of Human Anterior Cruciate Ligament (ACL) and ACL Graft Tissues*; in "Knee Ligaments: Structure, Function, Injury, and Repair", edited by D.M. Daniel, W.H. Akeson, and J.J. O'Connor; Raven Press, Ltd.; New York; Ch. 13; pp. 279-289; 1990.

Woo et al.; *Fundamental Studies in Knee Ligament Mechanics*, in "Knee Ligaments: Structure, Function, Injury, and Repair", edited by D.M.Daniel, W.H. Akeson, and J.J. O'Connor; Raven Press, Ltd.; New York; Ch. 7; pp. 115-134; 1990.

Yasuda et al.; *Effects of initial graft tension on clinical outcome after anterior cruciate ligament reconstruction -Autogenous doubled hamstring tendons connected in series with polyester tapes*; Am. J. Sports Med., 25; pp. 99-106; 1997.

Yoshiya et al.; *Graft tension in anterior cruciate ligament reconstruction: An in vivo study in dogs*; Am. J. Sports Med., 15; pp. 464-470; 1987.

Amiel et al.; *Ligament Structure, Chemistry, and Physiology*; in "Knee Ligaments: Structures, Function, Injury, and Repair", edited by D.M.Daniel, W.H. Akeson, and J.J. O'Connor, Raven Press, Ltd., New York; Ch.5, pp. 77-91; 1990.

Gertel eet al.; *Effect of anterior cruciate ligament graft tensioning direction, magnitude, and flexion angle on knee biomechanics*; Am. J. Sports Med., 21;4; pp. 572-581; 1993.

Harner et al.; *The effect of knee flexion angle and application of an anterior tibial load at the time of graft fixation on the biomechanics of a posterior cruciate ligament-reconstructed knee*; Am. J.Sports Med., 28:4; pp. 460-465; 2000.

\* cited by examiner

METHOD AND DEVICE FOR DETERMINING TENSION IN LIGAMENTS AND TENDONS

This application claims the benefit of U.S. Provisional Application No. 60/424,690, filed Nov. 8, 2002.

BACKGROUND OF THE INVENTION

This invention relates to the sensing of tension in such tissue as ligaments, tendons, muscle, and skin.

There are few common elective orthopedic procedures that have as many marginal results and complications as knee ligament surgery. The goal of knee surgery is to restore the normal kinematics of the knee. There are no universal protocols for ligament fixation. Setting a proper tension in a repaired or grafted ligament is important in the success of knee repair and the return of the patient to pre-injury activity levels. To regain normal anteroposterior translation, proper tension needs to be applied on the graft. If the tension is too low, the joint will be wobbly. If the tension is too high, the range of motion of the joint will be restricted, resulting in abnormal stress on the articular cartilage and the menisci. Excessive tension also interferes with the revascularization of the graft.

During knee surgery, the position of the knee and the load applied to the graft are dependent on the preference and experience of the surgeon. It has been suggested that graft fixation with a full extension may over-constrain the knee and that fixation at flexion and an anterior tibial load would best restore knee biomechanics. Applying graft tension at extension and checking the tension at 20° of flexion seems to be the norm. The strain value of the ligament or tendon is a macroscopic measure of the deformation. It is computed by dividing the change in length of the ligament or tendon by the unstressed length and is usually expressed as a percentage. Peak strain measured in vivo in the human anterior cruciate ligament (ACL) is about 4.4% (B. D. Beynnon and B. C. Fleming, Anterior cruciate ligament strain in-vivo: A review of previous work, Journal of Biomechanics, 31, 519-525, 1998). A high initial ACL tension (up to 80 N) may reduce the postoperative anterior laxity of the knee.

Ligaments consist of densely packed collagen fiber bundles arrayed in parallel along the length of the tissue. There are varying amounts of folding or crimp in the collagen fibrils, allowing for increasing resistance to increasing loads. Recruitment of additional fibrils occurs with increasing deformation under load. As the number of load-bearing fibrils increases, an increase in tissue stiffness results. The two major functions of the knee ligaments are to provide dynamic guide for knee motion and mechanical restraint to prevent abnormal translations. Knee instability may result in giving way under stress, re-injury of the knee, and early degenerative arthritis. The ultimate load of about 1725±269 N and the stiffness of about 182±33 N/mm are considered the gold standards.

The ACL is the most frequently injured ligament. It is composed of fascicular subunits within larger functional bands. The bands are selectively recruited during tensile loading. Fiber recruitment is due to the specific location of the insertions of the ACL on the tibia and the femur as different fibers attach to different locations on each bone. The fibers change length by a straightening of the crimp. The core of the ACL is the tension-carrying fibrous collagen. The ACL contains viscoelastic elements, blood vessels, nerves, and fibroblasts. The choice of graft for the replacement of ACL is controversial; prosthetic ligaments appear to result in more complications than autografts. Since strength is a major consideration in the selection of the graft, the two most common grafts are the central third of the patellar ligament and the hamstring tendon. For the first two months after implantation, the main factor affecting the structural strength of either graft is not the load-bearing capacity of the tissue but the point of fixation of the graft to the bone. The tendon tissues seem to lose some strength during the early healing period. Proper placement of the tunnels in the femur and the tibia during ACL reconstruction is important in minimizing permanent stretching of the graft.

The objective of tensioning the graft is to establish and maintain normal stability of the joint by eliminating wobble and restoring movement to the normal range. It has been shown that the initial forces in a graft are greatest near extension when tension is applied to the graft from its proximal end with the knee at 30° of flexion, and the forces in the graft may decrease by as much as 30% soon after fixation unless the graft has been cyclically preconditioned.

Ligaments and tendons function over a relatively small range of strain, typically less than 8% of its unstressed length. Joints have at least two ligaments that work opposed to each other to keep motion in the normal range. The human body has more than 1,000 ligaments and tendons. These tissues control the kinetic and kinematic actions of joints. The stress-strain relation of these tissues allows bones to move smoothly under low stress and limits the motion of the bones under high stress. Ligaments stabilize joints and guide them through smooth motions. Tendons transmit the dynamic forces generated by muscles across joints.

Ligaments contain water, elastin, proteoglycans, and packed collagen fibers that run parallel to the longitudinal axis of the ligament. The proteoglycans and water provide lubrication and spacing needed for the gliding function of joints. Collagen fibers in ligaments are arranged in varying degrees of crimp such that an increase in tensile force, a force directed along the axis of the ligament, results in the recruitment of more fibers to resist the load.

Ligaments and tendons are ordered structures. The collagen fibers lie parallel to the ligament (or tendon) axis displaying a cylindrical axis of symmetry. The motion of the atoms comprising any material matter such as collagen can be characterized by a collection of fundamental modes of vibration. Depending on the symmetry of the molecule, some normal modes of vibration may interact with optical radiation. One takes advantage of these optically active modes of vibration to characterize properties of the molecule. These vibrational modes can be investigated using either absorption spectroscopy method if the vibration has a permanent dipole moment and/or Raman spectroscopy if the vibration results in a change in "differential polarizability," i.e., the change in polarizability due to the motion of atoms involved in the vibration.

When stress is applied to the ligament, it is distributed through the entire structure of the ligament. The effect of the stress on vibrations along the direction of the stress is different from that on the vibrations whose motion is normal to the applied stress. In a very simplified model, one can think of the vibration as a simple oscillator governed by an effective mass and a force constant. The effect of the stress is to change the value of the force constant. Changes in the frequencies of the vibrations whose motion is along the axis of symmetry of the ligament or tendon are expected when the ligament or tendon is under stress. Due to the low frequency, between 500 $cm^{-1}$ and 2000 $cm^{-1}$, of the vibrational modes, the absorption spectrum of the ligament lies between 5 and 20 µm, a region where optical fibers are not readily available.

Needs exist for improved methods and devices for determining proper tensions in ligaments, tendons and other tissues.

SUMMARY OF THE INVENTION

The preferred embodiment of the present invention utilizes Infrared and Raman spectroscopy methods to assess the tension of ligaments, tendons and other tissues.

The tension measuring device of the present invention is used on a variety of tissue samples. Tension may be determined in tissues such as fibers, in vivo tissues, in vitro tissues, and in grafted tissue in animals and humans.

The device includes an electromagnetic radiation source for directing radiation energy onto a sample, either directly or using a probe. Between the photon source and the sample, emitted electromagnetic energies pass through a first filtering device. After passing the filtering devices, the emitted photons are then redirected by optical components, such as mirrors, lenses or optical fibers, onto the sample.

After impacting the tissue, scattered emissions are collected by a collecting means such as a collecting lens or optical fibers. The scattered emissions then pass through a second filtering device, such as an optical filter, and focused onto a spectrum analyzing device, such as a spectrometer. A photon detection device measures the scattered emissions. The tension in the tissue is obtained from the analysis of the scattered emissions by using a computing device such as a computer or a microprocessor. The analysis process utilizes Raman spectroscopy.

The photon source is preferably an infrared laser, with wavelength longer than 700 nm. However, visible light lasers and broadband infrared sources are also useful. A broadband infrared source, from 1 to 10 micrometers, requires use of IR absorption spectroscopy to determine tension in tissues, in vivo tissue and in vitro tissue.

The spectrometer is a scanning spectrometer with a point detector, where the point detector is a photomultiplier tube or a photodiode. The spectrometer may also be a non-scanning spectrometer using any array detector.

The first filter is a narrow bandpass filter centered at the photon source wavelength. The first filter eliminates fluorescent, plasma lines and other laser lines from the photon source emission beam. The second filter is a photon source blocking filter used to reduce the intensity of Raleigh-scattered light.

The computer or microprocessor controls the spectrometer scan speed and provides a display of the Raman spectroscopy. Raman spectroscopy is used to examine the relation between applied stress and tension in a graft during the conditioning of the tissue prior to implantation.

For clinical applications, a back-scattered geometry is preferred. However, other geometries may also be used.

These and further and other objects and features of the invention are apparent in the disclosure, which includes the above and ongoing written specification, with the drawings.

DETAILED DESCRIPTION OF THE PREFERRED EMBODIMENTS

The preferred embodiment of the present invention utilizes the Raman spectroscopy method to assess the tension of ligaments.

Raman Spectroscopy

The Raman effect is the scattering of electromagnetic radiation by a molecule with a change in frequency of the radiation and a change in energy level of the molecule. The difference between Raman scattering and fluorescence is illustrated in the energy level diagram shown in FIG. 1. The ground electronic state is assumed to consist of four vibrational levels. The sample molecule is assumed to be in the ground electronic state. When a photon is incident on the molecule, both Raman scattering and fluorescence may occur. The Raman scattering processes A1, A2, S1, and S2 all involve a virtual state of the molecule. Processes A1 and A2 are anti-Stokes Raman scattering with vibrational quantum number changes of v=1 (starting from the vibrational quantum number 0, the lowest vibrational level, of the ground electronic state to the virtual state and ending at the vibrational quantum number 1 of the ground state) and 2 (starting from the vibrational quantum number 0 of the ground electronic state to the virtual state and ending at the vibrational quantum number 2 of the ground state), respectively. The A1 and A2 processes result in the final state of the molecule being at a higher energy level than the initial state. Processes S1 and S2 are Stokes Raman scattering where the final state of the molecule is at a lower energy level than the initial state.

The S1 process starts from the vibrational level of v=2 of the ground electronic state. A photon is absorbed by the molecule resulting in a transition to a virtual intermediate state. A photon with different energy from that of the absorbed photon is emitted and the molecule transitions to the v=1 vibrational level of the ground electronic state. Likewise, the S2 process starts from the vibrational level of v=2 of the ground electronic state. A photon with different energy from that of the incident photon is emitted and the molecule transitions to the v=0 vibrational level of the electronic state.

Figure 1:
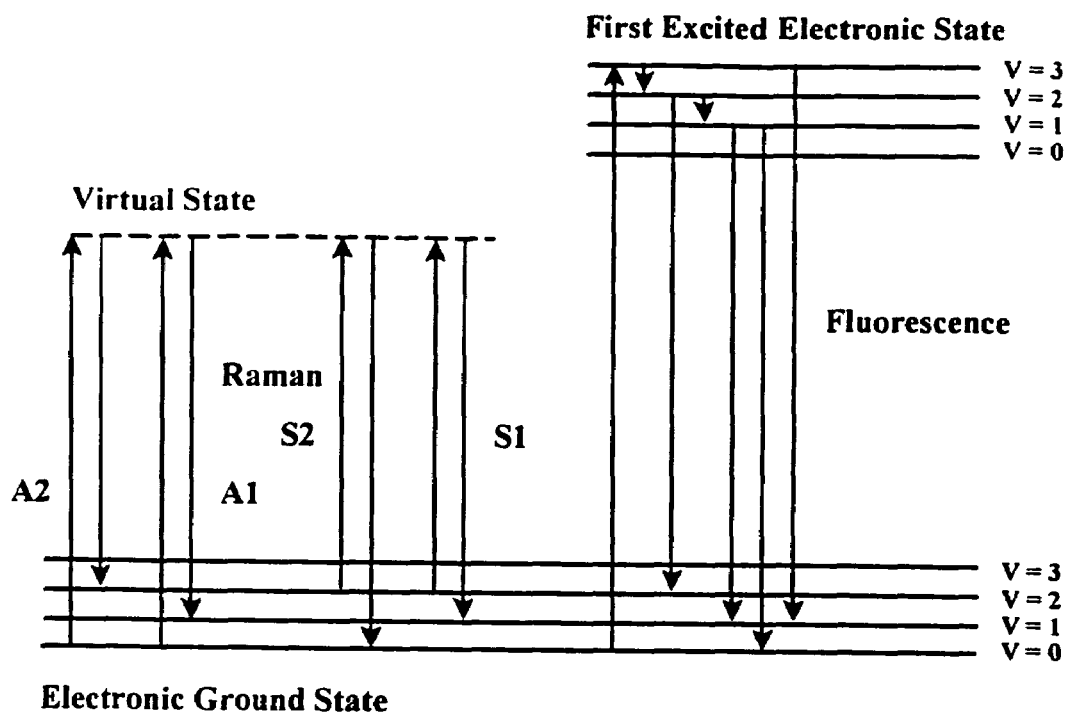
FIG. 1 is a schematic diagram illustrating the Raman and the fluorescence processes originating from the same electronic ground state. The Raman processes, such as A1, A2, S1, and S2, all involve a virtual state whereas the fluorescence processes involve a real electronic state, and in this case, the first excited electronic state.

Fluorescence can involve many possible transitions, some of which may be nonradiative, as shown in FIG. 1. As in the ground electronic state, the first excited electronic state of the molecule is also assumed to consist of four vibrational levels. Unlike Raman processes, all states involved in the fluorescent processes are actual states of the molecule.

While the Raman effect may appear to be similar to fluorescence, there are two distinct differences: (1) the Raman spectrum results in distinct spectral lines as compared with the continuum spectrum seen in fluorescence and (2) the lifetime of the Raman transition (equivalent to the lifetime of the virtual state) is approximately $10^{-12}$ sec while the fluorescence lifetime is much longer, typically $10^{-8}$ sec.

If the radiation of frequency $v_o$ is incident on a molecule in energy state $E_m$, the scattered radiation at frequency v can be written as:

$$v = v_o - (E_n - E)/h \tag{1}$$

where $E_n$ is another accessible energy state of the molecule and h is Planck's constant. Here the energy state $E_n$ may be higher or lower than $E_m$. A classical treatment of the Raman effect involves an examination of the polarizability tensor $\alpha$. The quantum theory of the Raman effect considers the absorption of the photon of frequency $v_0$ and the transition of the molecule from state m with energy $E_m$ to a virtual intermediate state followed by the emission of a photon of frequency v and the transition of the molecule to state n with energy $E_n$. The Raman shift defined as $|v_o-v|$ is characteristic of the molecule being probed by the incident radiation. When $v<v_o$ (Stokes scattering), the energy level of the molecule increases, since the molecule absorbs a photon with greater energy than the photon that the molecule emits. The increased internal energy may take the form of rotational, vibrational, or electronic energy or some combination of the three. When $v>v_o$ (anti-Stokes scattering) the energy of the molecule decreases, since the molecule emits a photon with greater energy than the photon that the molecule absorbs. Selection rules based on the symmetry of the molecular species can be used to determine which vibrations of the molecule are Raman-active.

Raman spectroscopy provides a more convenient means of measuring the tension in a tissue than the method of attaching a transducer to the ligament. The Raman technique is less intrusive and can be used as the joint is flexed or extended. It may be used with an endoscope to measure the tension in tissue such as ligaments and tendons during arthroscopic procedures. This information can be used by the surgeons to decide what surgical corrections should be performed. A minimally obtrusive Raman probe for measuring ligament tension independent of joint position over the full range from extension to flexion would improve the surgeon's ability to restore the full range of motion of the joint.

Raman Spectra of Collagen

The major features of the Raman spectrum of collagen have been assigned to internal vibrations of individual amino acids, especially hydroxyproline which is present in collagen at high concentrations and serves as a crosslink between the triple helixes of the collagen molecule. At Raman shifts less than 1000 $cm^{-1}$, the vibrations between the adjacent carbon atoms of the backbone, and between the hydroxyproline and proline rings account for the Raman spectrum.

At larger shifts, the Raman lines correspond to vibrational contributions of molecular subunits such as $CH_3$, $NH_3^+$, C—N, and the amide I and amide III. Strong Raman lines are located at 1248 $cm^{-1}$ (amide III), 1271 $cm^{-1}$ (amide III), 1451 $cm^{-1}$ (bending of adjacent $CH_3$ subunits), and 1671 $cm^{-1}$ (amide I). The amide groups and the hydroxyproline ring exhibit levels of compression, their Raman lines shift to higher wave numbers. The amide I vibrations are characterized by carbonyl stretching and N—H in-plane bending. The carbonyl group is almost perpendicular to the collagen axis (the direction of the stress), the bonds are subject to compression. An in-plane C—N vibration that is laterally compressed when the structure is deformed under stress characterizes the amide III vibration.

In preliminary in vitro measurements, a bovine ligament is used as the sample. Sutures are placed at each end of the ligament and the ligament is mounted vertically between two horizontal rods, with the sutures looped around the rods to secure the sample. Light from a laser, such as, but not limited to, a Helium-Neon laser operating at 0.6328 μm is focused onto the ligament using a focusing lens. A laser line filter centered at 0.6328 μm with a full-width-half-maximum of 0.001 μm is used to eliminate the laser plasma lines from the incident radiation. Optical radiation scattered at 90° to a plane defined by the ligament axis and the wave vector of the incident beam is collected using a lens and focused onto the entrance slit of a monochromator. A photodetector, such as a photomultiplier tube measures the intensity of the scattered radiation as a function of wavelength.

Raman spectra of the ligament sample may be measured at increasing strain by pulling the top rod higher while keeping the bottom rod at a fixed location.

To distinguish the Raman signals from grating "ghosts," i.e., spectral lines that are due to the deviations in the periodicity of the grating used in the spectrometer, the grating ghosts are identified by measuring laser radiation scattered from a polished metal rod.

A preferred embodiment is a design of a device for measuring stress conditions of a ligament. It consists of, but is not limited to, a photon source such as a laser, an optical probe consisting of two optical fibers, a spectrometer with a detector, and a control unit. The probe is placed in contact with the ligament or tendon. Laser light is transmitted to the tissue via the illumination fiber. Scattered light is collected via the collection fiber and focused onto the entrance slit of the spectrometer. The output of the spectrometer is displayed on the control unit.

Figure 2:
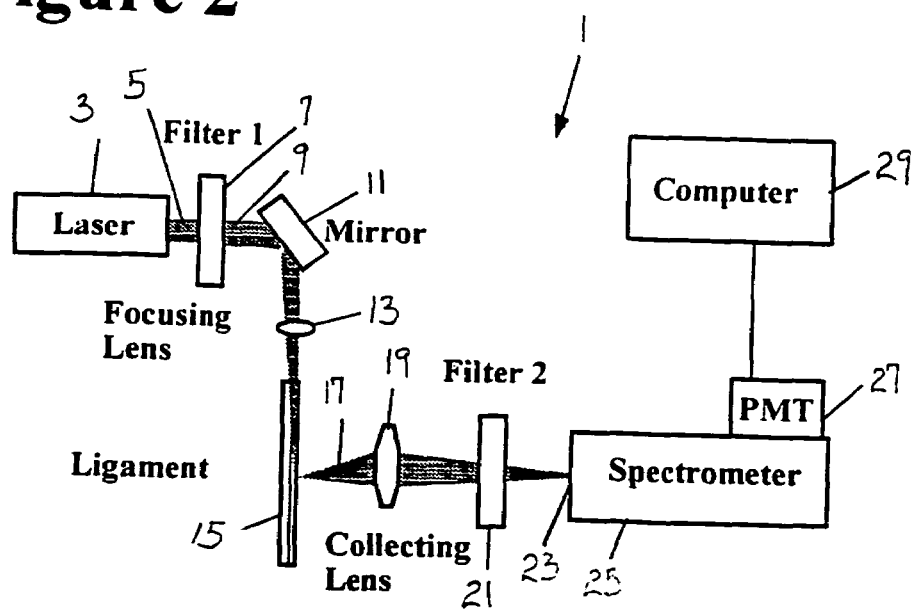
FIG. 2 is a schematic diagram of an embodiment of the tension measuring apparatus constructed in accordance with the present invention.

A diagram of the detection apparatus 1 is shown in FIG. 2. The electromagnetic radiation output 5 of a laser 3 may be directed to a sample 15 either directly or using a probe. The photons 5 pass through a narrow bandpass filtering device 7 centered at the laser wavelength. This filter 7 eliminates other emissions (fluorescence, plasma lines, laser lines and other unwanted electromagnetic radiation) from the excitation beam. Both a He—Ne (632.8 nm) and the GaAs (793 nm) (as well as any other) lasers can be used in the measurements. The higher energy photons of the He—Ne laser due to the shorter wavelength result in fluorescence of the tissue. By using the longer wavelength GaAs laser the amount of fluorescence is reduced. The filtered laser beam 9 is focused onto the tissue 15 using a system of optical components, such as a turning mirror 11 and a focusing lens 13 or optical fibers.

The light 17 scattered by the tissue 15 is collected by a collecting means, such as a lens 19 or an optical fiber. The scattered emissions 17 then pass through a second filtering device 21 and are focused on the input slit 23 of a spectrum analyzing device 25. The second filtering device 21 is a laser blocking filter used to reduce the intensity of the Rayleigh-scattered light. The spectrometer 25 has a 1200 mm/inch grating blazed at 750 nm. A photodetector 27 is used to measure the signal. A computer or microprocessor 29 that collects the output current from the photodetector 27 also controls the spectrometer 25 scan speed. Other geometries besides the 90° geometry shown in FIG. 2 can also be used for data collection. For clinical applications, a back-scattered geometry would provide a more compact design to the apparatus. The ligament 15 is mounted in a holder that allows the stress to be increased.

Figure 3:
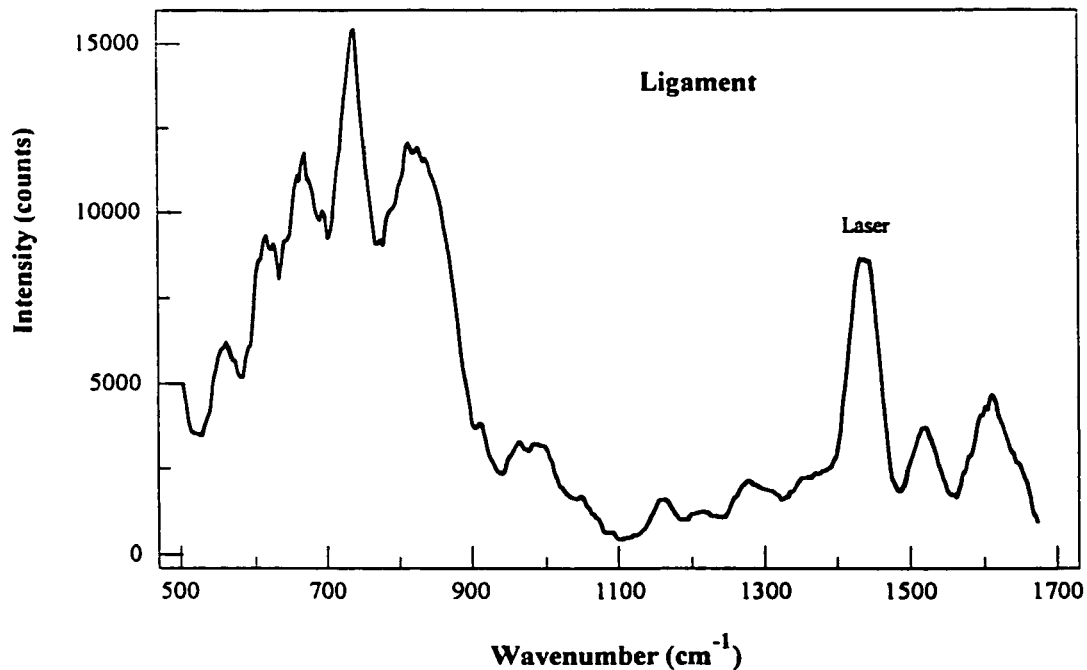
FIG. 3 shows the Raman spectrum of an unstressed bovine ligament obtained using the 793 nm laser and a 90° geometry.

The Raman spectrum of an unstressed bovine ligament obtained using the 793 nm laser and a 90° geometry is shown in FIG. 3. The Raman lines are due to vibrations of the collagen backbone and internal vibrations of the amino acids constituting the collagen molecule. The Raman data were obtained from whole bovine ligaments and bovine tendons, not individual fibers. Sutures are used to fasten the samples in a mount. Stress is applied to the sample by moving one end of the mount. As the stress increases, both positive and negative changes in the Raman shift of the spectral features are observed. The decrease in Raman shift with increasing stress is observed in the vibrations associated with the collagen backbone. The vibrations, which exhibit an increase in Raman shift with increasing stress, are associated with amino acid residues attached to the collagen backbone.

Figure 4:
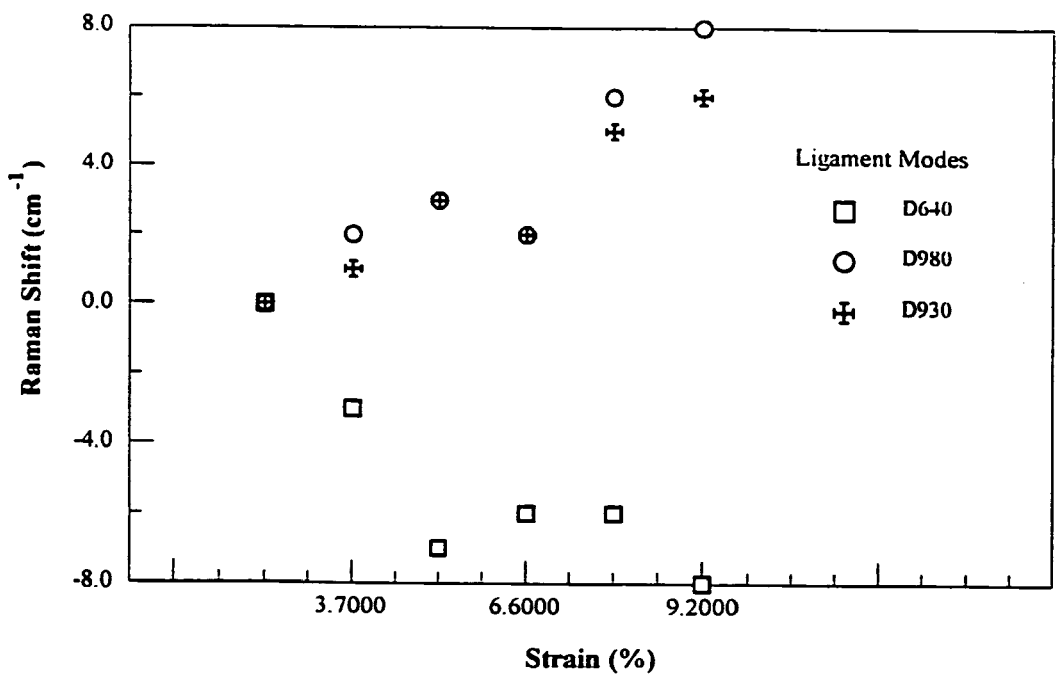
FIG. 4 shows the change in Raman shift of three collagen vibrations for values of strain between 0% and 9.3%.

FIG. 4 shows the change in Raman shift of three collagen vibrations for values of strain between 0% and 9.3%. FIG. 4 shows a total of 18 data points. The left most point corresponds to the unstressed condition (0% strain). It provides a reference level for determining the change in Raman shift as strain increases. This point serves as a starting point for analyzing the change in Raman shift for the three different vibrations. The three Raman lines expressed in FIG. 4 include a C-C stretching vibration at 830 $cm^{-1}$, an amide I vibration at 960 $cm^{-1}$, and an internal phenylalanine vibration at 630 $cm^{-1}$.

Figure 5:
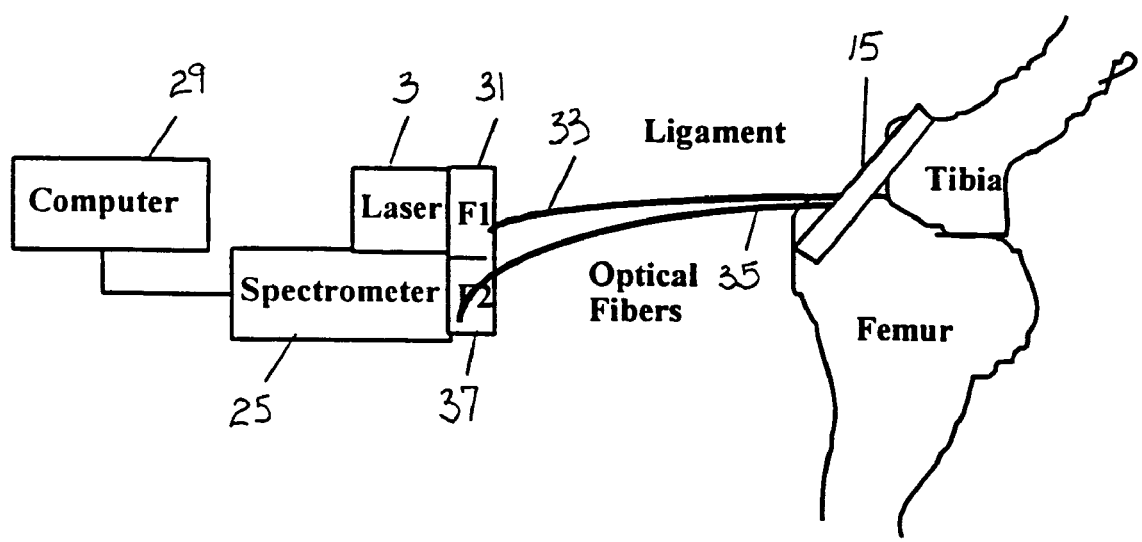
FIG. 5 shows major components of a tension measuring apparatus.

The major components of a tension measuring apparatus are shown in FIG. 5. A laser 3 is used as a source of exciting radiation. The laser output is filtered using a narrow band filter 31 centered on the laser line. The beam is then coupled into an optical fiber 33 and delivered to the surface of the tissue 15. In FIG. 5, the tissue 15 is a knee ligament linking the tibia and the femur. The scattered light is collected using a second optical fiber 35. A laser blocking filter 37 is inserted between the second fiber 35 and the entrance slit 23 to a spectrometer 25. Either a scanning or a nonscanning spectrometer 25 may be used. The output of the spectrometer 25 detector is transferred to a computer or microprocessor 29 for processing and display. FIG. 5 shows a backscattering geometry for compactness such as preferred in a clinical environment. The apparatus of the present invention does not need to be a backscattering geometry. The two optical fibers used to excite the tissue and collect the scattered light may be placed in an endoscope. The Raman shifts of the primary lines of interest for tension measurement range from approximately 600 $cm^{-1}$ to 1700 $cm^{-1}$. Using an excitation source of 785 nm, this corresponds to a wavelength region of 825 nm to 910 nm.

The preliminary measurements demonstrated the utility of using a near-IR laser as the excitation source. The minimization of the tissue fluorescence improves the signal to noise ratio of the Raman spectrum. Our measurements were obtained using a low power GaAs diode laser operating at 793 nm. To improve the speed of data acquisition and the signal to noise of the Raman spectrum, a higher power laser may be used.

Tension Algorithm

Conditioning ligaments prior to implantation has been shown to decrease the relaxation of the ligament that occurs soon after implantation. The conditioning is applied by either applying a stress to the graft for a fixed amount of time or cycling the graft between stressed and unstressed states a fixed number of times.

The data have shown decreasing Raman shifts associated with the C—C stretching vibrations of the collagen backbone. The change in Raman shift with tension follows a near linear relation that can be used to compute tension. The tension of the ligament can be obtained from an analysis of two or more of the frequency shifted Raman lines. The tension can be expressed in the form:

$$T(\Delta v) = T_0 + C_1 \Delta v + C_2 (\Delta v)^2 \quad (2)$$

where $C_1$ and $C_2$ are coefficients obtained from a fitting of Equation (2) to the experimental data. The coefficients $C_1$ and $C_2$ can be determined by fitting data obtained during the ligament conditioning process to Equation (2). The invention can be used to measure the tension in the graft as the ends are secured into the bone attachment sites. The tension of the fixed graft is determined from Equation (2) using measurements of the Raman spectrum and the previously determined coefficients $C_1$ and $C_2$. The ligament tension can be calculated by averaging the tension values obtained with each Raman line.

While the invention has been described with reference to specific embodiments, modifications and variations of the invention may be constructed without departing from the scope of the invention.

The invention claimed is:

1. A method of determining tension in tissues comprising:
providing a sample tissue for analysis,
providing a photon source,
providing a means of delivering an incident photon energy and a means of delivering collected photon energy,
providing an optical probe for placing in optical contact with the tissue sample,
passing photon source emissions through a first filter and onto a mirror,
redirecting the photon source emissions off the mirror, through a focusing lens and onto the sample,
collecting first and second scattered emissions from the tissue in a collecting lens,
passing the first and second scattered emissions through a second filter and into a spectrometer,
measuring the first and second scattered emissions with a photodetector,
analyzing the first and second scattered emissions with a computing device and determining peaks, and
calculating and outputting the tension in the tissue by analyzing frequency shifts in the peaks of the first and second scattered emissions.

2. The method of claim 1, wherein tension is determined in fiber tissues.

3. The method of claim 1, wherein tension is determined in vivo in tissues.

4. The method of claim 1, wherein tension is determined in vitro in tissues.

5. The method of claim 1, wherein tension is determined in grafted tissue in animals and humans.

6. The method of claim 1, wherein providing the photon source comprises providing an infrared laser, with wavelengths longer than 700 nm.

7. The method of claim 1, wherein providing the photon source is comprises providing a visible light laser.

8. The method of claim 1, wherein the photon source is a broadband infrared source, from 1 to 10 micrometers, and further comprising using IR absorption spectroscopy to determine tension in tissues selected from a group consisting of in vivo tissues and in vitro tissues.

9. The method of claim 1, wherein passing the scattered emissions through the spectrometer comprises passing through a scanning spectrometer.

10. The method of claim 9, wherein passing through the scanning spectrometer comprises passing through a point detector.

11. The method of claim 10, wherein passing through the point detector comprises passing through a photomultiplier tube.

12. The method of claim 10, wherein passing through the point detector comprises passing through a photodiode.

13. The method of claim 1, wherein passing the scattered emissions through the spectrometer comprises passing though a non-scanning spectrometer.

14. The method of claim 13, wherein passing through the non-scanning spectrometer comprises passing through an array detector.

15. The method of claim 1, wherein passing through the first filter comprises passing through a narrow bandpass filter centered at the photon source wavelength.

16. The method of claim 1, wherein passing through the first filter comprises eliminating fluorescent, plasma lines, laser lines and other undesired electromagnetic radiation from the photon source emission beam.

17. The method of claim 1, wherein passing the scattered emissions through the second filter comprises passing through a photon source blocking filter used to reduce the intensity of Raleigh-scattered light.

18. The method of claim 1, wherein the computer controls the spectrometer scan speed.

19. The method of claim 1, wherein the outputting comprises computer displays of the calculated tension.

20. The method of claim 1, further comprising using Raman spectroscopy for examining the relation between applied stress and tension in a graft during the conditioning of the tissue prior to implantation.

21. The method of claim 1, further comprising displaying the calculated tension.

22. The method of claim 1, further comprising securing the tissue into bone attachment sites, wherein the tension is calculated as the tissue is secured into bone attachment sites.

23. A method of measuring tension in ligaments or tendons comprising:
    illuminating a ligament or tendon with electromagnetic radiation thereby reflecting and scattering electromagnetic radiation from the ligament or tendon,
    collecting the scattered electromagnetic radiation with a collecting means,
    detecting Raman scattered electromagnetic radiation,
    receiving the Raman scattered electromagnetic radiation from the collecting means in a spectrometer,
    analyzing the Raman scattered electromagnetic radiation,
    computing the effects of Raman scattering induced by tension in the ligament or tendon by determining peaks and
    calculating the tension in the tissue from analysis of two or more frequency shifted peaks.

24. An apparatus for determining tension in tissues comprising:
    a photon source for directing energy onto a sample, wherein photons are emitted and passed through a first filter and onto a mirror, the photons are then redirected by the mirror through a focusing lens and onto the sample,
    a means of delivering an incident photon energy and a means of delivering collected photon energy,
    a collecting lens for collecting scattered emissions from the sample,
    a second filter for receiving the scattered emission from the collecting lens,
    a spectrometer for receiving the scattered emissions from the second filter,
    a photodetector for measuring the scattered emissions,
    a computer programmed for measuring and analyzing tension in the tissue by calculations from analyses of two or more frequency shifts using Raman spectroscopy, and
    a display showing tension in the sample.

25. The apparatus of claim 24, wherein the photon source is an infrared laser, with wavelengths longer than 700 nm.

26. The apparatus of claim 24, wherein the photon source is a visible light laser.

27. The apparatus of claim 24, wherein the photon source is a broadband infrared source, from 1 to 10 micrometers, and further comprising determining with IR absorption spectroscopy tension in tissues, in vivo tissue and in vitro tissue.

28. The apparatus of claim 24, wherein the spectrometer is a scanning spectrometer.

29. The apparatus of claim 28, wherein the scanning spectrometer comprises a point detector.

30. The apparatus of claim 29, wherein the point detector is a photomultiplier tube.

31. The apparatus of claim 29, wherein the point detector is a photodiode.

32. The apparatus of claim 24, wherein the spectrometer is a non-scanning spectrometer.

33. The apparatus of claim 32, wherein the non-scamming spectrometer comprises an array detector.

34. The apparatus of claim 24, wherein the first filter is a narrow bandpass filter centered at the photon source wavelength.

35. The apparatus of claim 24, wherein the first filter eliminates fluorescent, plasma lines, laser lines and other undesired electromagnetic radiation from the photon source emission beam.

36. The apparatus of claim 24, wherein the second filter is a photon source blocking filter used to reduce the intensity of Raleigh-scattered light.

37. The apparatus of claim 24, wherein the computer controls the spectrometer scan speed.

38. The apparatus of claim 24, further comprising computer displays of the results of Raman spectroscopy.

39. The apparatus of claim 38, wherein the results of the Raman spectroscopy provide the relation between applied stress and tension in a graft during the conditioning of the sample prior to implantation.

40. The apparatus of claim 24, further comprising a display for displaying the calculated tension.

41. An apparatus for determining tension in ligaments and tendons, comprising:
    a source for supplying an electromagnetic incident beam on a sample ligament or tendon,
    a receiver for collecting and receiving reflected and first and second Raman scattered electromagnetic emissions from the sample ligament or tendon,
    a spectrometer and a photodetector connected to the receiver for detecting and analyzing the first and second Raman scattered electromagnetic emissions,
    a computer or microprocessor programmed for evaluating the first and second Raman scattered electromagnetic emissions to determine peaks and calculating an output corresponding to tension in the ligament or tendon from an analysis of a frequency shift of the peaks, and
    a display for displaying the output.

42. The apparatus of claim 41, further comprising a display for displaying the calculated tension.

\* \* \* \* \*